United States Patent
Oh et al.

(10) Patent No.: US 12,308,388 B2
(45) Date of Patent: May 20, 2025

(54) ELECTROLYTE SOLUTION ADDITIVE FOR SECONDARY BATTERY, AND NON-AQUEOUS ELECTROLYTE SOLUTION FOR LITHIUM SECONDARY BATTERY AND LITHIUM SECONDARY BATTERY WHICH INCLUDE THE SAME

(71) Applicant: LG Energy Solution, Ltd., Seoul (KR)

(72) Inventors: Jeong Woo Oh, Daejeon (KR); Yoo Sun Kang, Daejeon (KR); Chul Haeng Lee, Daejeon (KR)

(73) Assignee: LG Energy Solution, Ltd., Seoul (KR)

(*) Notice: Subject to any disclaimer, the term of this patent is extended or adjusted under 35 U.S.C. 154(b) by 516 days.

(21) Appl. No.: 17/771,911

(22) PCT Filed: Mar. 23, 2021

(86) PCT No.: PCT/KR2021/003574
§ 371 (c)(1),
(2) Date: Apr. 26, 2022

(87) PCT Pub. No.: WO2021/194220
PCT Pub. Date: Sep. 30, 2021

(65) Prior Publication Data
US 2023/0006251 A1   Jan. 5, 2023

(30) Foreign Application Priority Data

Mar. 26, 2020 (KR) .................. 10-2020-0036576

(51) Int. Cl.
| | | |
|---|---|---|
| *H01M 10/0567* | (2010.01) | |
| *C07D 285/12* | (2006.01) | |
| *H01M 10/0525* | (2010.01) | |
| *H01M 10/0569* | (2010.01) | |

(52) U.S. Cl.
CPC ...... *H01M 10/0567* (2013.01); *C07D 285/12* (2013.01); *H01M 10/0525* (2013.01); *H01M 10/0569* (2013.01); *H01M 2300/0028* (2013.01)

(58) Field of Classification Search
CPC ......... H01M 10/0525; H01M 10/0567; H01M 10/0569; H01M 2300/0028; H01M 2300/0037; C07D 285/12; C07D 285/135; Y02E 60/10
See application file for complete search history.

(56) References Cited

U.S. PATENT DOCUMENTS

| | | |
|---|---|---|
| 6,340,539 B1 | 1/2002 | Yamaguchi et al. |
| 2005/0042520 A1 | 2/2005 | Roh et al. |
| 2006/0016472 A1 | 1/2006 | Park et al. |
| 2014/0120424 A1 | 5/2014 | Yamada et al. |
| 2014/0199593 A1 | 7/2014 | Hotta et al. |
| 2015/0045928 A1 | 2/2015 | Perez et al. |
| 2015/0086668 A1 | 3/2015 | Perez et al. |
| 2016/0083849 A1 | 3/2016 | Morris et al. |
| 2016/0248114 A1 | 8/2016 | Huskinson et al. |
| 2017/0037207 A1 | 2/2017 | Kunita et al. |
| 2018/0083321 A1 | 3/2018 | Hotta et al. |
| 2019/0148772 A1 | 5/2019 | Park et al. |
| 2020/0354837 A1 | 11/2020 | Morris et al. |
| 2021/0083311 A1 | 3/2021 | Huskinson et al. |
| 2022/0380904 A1 | 12/2022 | Morris |

FOREIGN PATENT DOCUMENTS

| | | |
|---|---|---|
| CN | 103620816 A | 3/2014 |
| CN | 106133976 A | 11/2016 |
| CN | 109786828 A | 5/2019 |
| EP | 1069119 B1 | 9/2004 |
| JP | H06-310173 A | 11/1994 |
| JP | H10321233 A | 12/1998 |
| JP | 2009117081 A | 5/2009 |
| JP | 4555164 B2 | 9/2010 |
| JP | 5285082 B2 | 9/2013 |
| JP | 2014-130774 A | 7/2014 |
| JP | 2015-128076 A | 7/2015 |

(Continued)

OTHER PUBLICATIONS

Rafiquee,M.Z.A., et al.,"Influence of Some Thiadiazole Derivatives on Corrosion Inhibition of Mild Steel in Formic and Acetic Acid Media", Portugaliae Electrochimica Acta 25 ( Apr. 2007) pp. 419-434.
International Search Report for Application No. PCT/KR2021/003574 mailed Jun. 24, 2021, pp. 1-3.
Zheng W et al: "Structure-activity relationship study of a novel necroptosis inhibitor, necrostatin-7", Bioorganic & Medicinal Chemistry Letters, Elsevier, Amsterdam NL, vol. 18, No. 18, Sep. 15, 2008 (Sep. 15, 2008), pp. 4932-4935, xp025407642.

(Continued)

*Primary Examiner* — Victoria H Lynch
(74) *Attorney, Agent, or Firm* — Lerner David LLP

(57) ABSTRACT

An electrolyte solution additive, an electrolyte solution including the same, and a lithium secondary battery including the same are disclosed herein. In some embodiments, an electrolyte solution additive includes a compound represented by Formula 1:

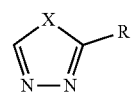

[Formula 1]

Wherein X is oxygen (O) or sulfur (S), and R is a substituted or unsubstituted alkyl group having 1 to 5 carbon atoms or $N(R_1)_2$, wherein $R_1$ is hydrogen or a substituted or unsubstituted alkyl group having 1 to 5 carbon atoms. The additive has an excellent effect of scavenging a decomposition product generated from a lithium salt and simultaneously forming a robust film on a surface of a positive electrode.

9 Claims, No Drawings

(56) References Cited

FOREIGN PATENT DOCUMENTS

| | | |
|---|---|---|
| JP | 2017-033692 A | 2/2017 |
| KR | 20050122966 A | 12/2005 |
| KR | 100558846 B1 | 3/2006 |
| KR | 20070120592 A | 12/2007 |
| KR | 20160067882 A | 6/2016 |
| KR | 20180030744 A | 3/2018 |
| KR | 101883249 B1 | 8/2018 |
| WO | 8302368 A1 | 7/1983 |

OTHER PUBLICATIONS

Aoyama Toyohiko, et al., "New Method and Reagents in Oranic Synthesis. 53. Lithium Trimethylsilyldiazomethane: a New Synthon for the Preparation of 2-Amino-1,3,4-thiadiazoles from Isothiocyanates", Heterocycles, vol. 23, No. 9, Jan. 1, 1985 (Jan. 1, 1985), pp. 2367-2369, xp009551598.
Extended European Search Report for Application No. 21774668.4 dated Feb. 5, 2024. 7 pgs.
Search Report dated Jan. 29, 24 from Office Action for Chinese Application No. 202180006078.2 issued Feb. 2, 2024. 2 pgs.

ELECTROLYTE SOLUTION ADDITIVE FOR SECONDARY BATTERY, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

This application is a national phase entry under 35 U.S.C. § 371 of International Application No. PCT/KR2021/003574, filed on Mar. 23, 2021, which claims priority from Korean Patent Application No. 10-2020-0036576, filed on Mar. 26, 2020, the disclosures of which are incorporated by reference herein.

TECHNICAL FIELD

The present invention relates to an electrolyte solution additive for a secondary battery, and a non-aqueous electrolyte solution for a lithium secondary battery and a lithium secondary battery which include the same, and more particularly, to an electrolyte solution additive for a secondary battery which may suppress dissolution of transition metal during high-temperature storage, and a non-aqueous electrolyte solution for a lithium secondary battery and a lithium secondary battery which include the same.

BACKGROUND ART

There is a need to develop technology for efficiently storing and utilizing electrical energy as personal IT devices and computer networks are developed with the development of information society and the accompanying dependency of society as a whole on the electrical energy is increased.

Since a secondary battery may be miniaturized to be applicable to a personal IT device and may be applied to an electric vehicle and a power storage device, there emerges an interest in the secondary battery as the most suitable technology for various applications. Among these secondary batteries, a lithium-ion battery (LIB), which is a battery system having high energy density, is in the spotlight, and is currently being used in various devices.

The lithium-ion battery is generally composed of a positive electrode that includes a positive electrode active material formed of a transition metal oxide containing lithium, a negative electrode including a negative electrode active material capable of storing lithium ions, an electrolyte solution that becomes a medium for transferring lithium ions, and a separator.

The positive electrode stores energy through a redox reaction of transition metal, wherein this results in the fact that the transition metal must be essentially included in a positive electrode material. Also, the electrolyte solution is composed of a lithium salt, an organic solvent dissolving the lithium salt, and a functional additive, wherein proper selection of these components is important to improve electrochemical properties of the battery.

There is a disadvantage in that the transition metal is easily dissolved from the positive electrode into the electrolyte solution during charge and discharge or exposure to high temperatures. For example, since the lithium salt, typically $LiPF_6$, contained in the electrolyte solution is very vulnerable to heat, the lithium salt generates a Lewis acid, such as $PF_5$, while being thermally decomposed when the battery is exposed to high temperatures. The Lewis acid destructs a film formed on a surface of the electrode to easily dissolve the transition metals of the positive electrode into the electrolyte solution.

These dissolved transition metal ions become a cause of increasing resistance of the positive electrode while being re-deposited on the positive electrode, and, in contrast, cause additional consumption of lithium ions and an increase in resistance due to self-discharge of the negative electrode and destruction and regeneration of a solid electrolyte interphase (SEI) by being transferred to the negative electrode through the electrolyte solution and then electrodeposited on the negative electrode.

Thus, there is an urgent need to develop a method which may reduce degradation of the battery at high temperatures by scavenging by-products (HF and $PF_5$, etc.), which are generated by the thermal decomposition of the lithium salt, and simultaneously suppressing the dissolution of the transition metal from the positive electrode.

DISCLOSURE OF THE INVENTION

Technical Problem

An aspect of the present invention provides an electrolyte solution additive for a secondary battery which has an excellent effect of scavenging a decomposition product generated from a lithium salt and simultaneously forms a robust film on a surface of a positive electrode.

Another aspect of the present invention provides a non-aqueous electrolyte solution for a lithium secondary battery, which may achieve excellent high-temperature stability and high-temperature cycle characteristics by including the electrolyte solution additive for a secondary battery, and a lithium secondary battery including the same.

Technical Solution

According to an aspect of the present invention, there is provided an electrolyte solution additive for a secondary battery which includes a compound represented by the following Formula 1.

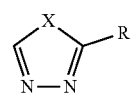

[Formula 1]

In Formula 1,

X is oxygen (O) or sulfur (S), and

R is a substituted or unsubstituted alkyl group having 1 to 5 carbon atoms or $N(R_1)_2$ where $R_1$ is hydrogen or a substituted or unsubstituted alkyl group having 1 to 5 carbon atoms.

According to another aspect of the present invention, there is provided a non-aqueous electrolyte solution for a lithium secondary battery which includes a lithium salt, an organic solvent, and the electrolyte solution additive for a secondary battery of the present invention as a first additive.

According to another aspect of the present invention, there is provided a lithium secondary battery which includes a positive electrode including a positive electrode active material; a negative electrode including a negative electrode active material; a separator disposed between the negative electrode and the positive electrode; and the non-aqueous electrolyte solution for a lithium secondary battery of the present invention.

Advantageous Effects

A compound represented by Formula 1, which is included as an additive in a non-aqueous electrolyte solution of the present invention, is a compound containing at least two nitrogen atoms having an unshared electron pair in its structure, wherein it may not only form a stable film on a surface of a positive electrode or negative electrode, but also may effectively scavenge a Lewis acid generated as a decomposition product of the electrolyte solution because the nitrogen atom acts as a Lewis base.

Thus, a non-aqueous electrolyte solution capable of suppressing additional decomposition of an organic solvent in the electrolyte solution and capable of effectively suppressing dissolution of transition metal from the positive electrode and a lithium secondary battery, in which high-temperature stability and high-temperature cycle characteristics are improved by including the same, may be achieved.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

Also, the terms used in the present specification are used to merely describe exemplary embodiments, but are not intended to limit the invention. The terms of a singular form may include plural forms unless referred to the contrary.

Before describing the present invention, it will be further understood that the terms "include," "comprise," or "have" in this specification specify the presence of stated features, numbers, steps, elements, or combinations thereof, but do not preclude the presence or addition of one or more other features, numbers, steps, elements, or combinations thereof.

The expressions "a" and "b" in the description of "a to b carbon atoms" in the present specification each denote the number of carbon atoms included in a specific functional group. That is, the functional group may include "a" to "b" carbon atoms. For example, the expression "alkylene group having 1 to 5 carbon atoms" denotes an alkylene group including 1 to 5 carbon atoms, that is, —CH$_2$—, —CH$_2$CH$_2$—, —CH$_2$CH$_2$CH$_2$—, —CH$_2$ (CH$_3$) CH—, —CH(CH$_3$) CH$_2$—, and —CH(CH$_3$) CH$_2$CH$_2$—.

The expression "alkylene group" denotes a branched or unbranched divalent unsaturated hydrocarbon group. In an embodiment, the alkylene group may be substituted or unsubstituted. The alkylene group may include a methylene group, an ethylene group, a propylene group, an isopropylene group, a butylene group, an isobutylene group, a tert-butylene group, a pentylene group, and 3-pentylene group.

Also, unless otherwise defined in the specification, the expression "substitution" denotes that at least one hydrogen bonded to carbon is substituted with an element other than hydrogen, for example, an alkyl group having 1 to 6 carbon atoms or fluorine.

In general, transition metals constituting a positive electrode may be easily dissolved in an electrolyte solution due to hydrogen fluoride (HF) generated from the electrolyte solution during battery operation or structural variation of the positive electrode according to repeated charge and discharge, and dissolved transition metal ions are re-deposited on the positive electrode to be a cause of increasing resistance of the positive electrode. Also, since the transition metals moved to a negative electrode through the electrolyte solution are electrodeposited on the negative electrode to self-discharge the negative electrode and destruct a solid electrolyte interphase (SEI) that gives passivation ability to the negative electrode, interfacial resistance of the negative electrode is increased by promoting an additional electrolyte solution decomposition reaction.

Since this series of reactions reduces an amount of available lithium ions in a battery, it not only leads to the degradation of capacity of the battery, but an electrolyte solution decomposition reaction is also accompanied, and thus, resistance is increased. In addition, in a case in which metal impurities are included in the electrode during configuration of the positive electrode, since the metal impurities are dissolved from the positive electrode during initial charge, metal ions thus dissolved are electrodeposited on a surface of the negative electrode. The electrodeposited metal ions become a major cause of low-voltage failure by growing into dendrites to cause an internal short circuit of the battery.

The present invention aims at providing a non-aqueous electrolyte solution for a lithium secondary battery, which includes an additive capable of suppressing the dissolution of the transition metal by forming a robust film on a surface of the positive electrode as well as preventing the electrodeposition on the negative electrode or positive electrode by scavenging the dissolved metal ions, a cause of such degradation and failure behavior, in the battery, and a lithium secondary battery including the same.

Electrolyte Solution Additive for Secondary Battery

In the present invention, provided is an electrolyte solution additive for a secondary battery which includes a compound represented by the following Formula 1.

[Formula 1]

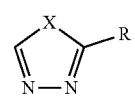

In Formula 1,
X is oxygen (O) or sulfur (S), and
R is a substituted or unsubstituted alkyl group having 1 to 5 carbon atoms or N(R$_1$)$_2$ where R$_1$ is hydrogen or a substituted or unsubstituted alkyl group having 1 to 5 carbon atoms.

Specifically, in Formula 1, X is S, and R may be a substituted or unsubstituted alkyl group having 1 to 3 carbon atoms or N(R$_1$)$_2$ where R$_1$ is hydrogen or a substituted or unsubstituted alkyl group having 1 to 3 carbon atoms.

Also, in Formula 1, X is S, and R may be N(R$_1$)$_2$ where R$_1$ is hydrogen or a substituted or unsubstituted alkyl group having 1 to 3 carbon atoms.

More specifically, the compound represented by Formula 1 may be a compound represented by Formula 1a below.

[Formula 1a]

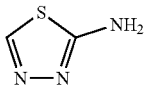

Since the compound represented by Formula 1 contains a nitrogen (N) atom-based unshared electron pair in its structure, it basically has a high binding force with a Lewis acid material. Thus, it may scavenge a by-product causing degradation of the secondary battery at high temperatures, for example, a decomposition product generated by thermal decomposition of a lithium salt, and it may prevent the resulting degradation of the film on the surface of the positive electrode to suppress the dissolution of the transition metal. In addition, the nitrogen (N) atom-based material may be electrochemically reductively decomposed to form a nitrogen (N) atom-based film (SEI) on the negative electrode. The nitrogen (N) atom-based film has a characteristic in which it is not easily decomposed and maintained when the battery is exposed to high temperatures. Thus, since the characteristic, in which the SEI is not decomposed and stably maintained on the surface of the negative electrode, is provided, a negative electrode reduction reaction of additional transition metals due to the decomposition of the SEI may be controlled and the re-deposition of the transition metal dissolved from the positive electrode during high-temperature storage on the negative electrode may be prevented.

In a case in which the compound of Formula 1 includes an amine group ($N(R_1)_2$) as a substituent (R), a more robust film may be formed on the surface of the positive electrode while an unshared electron pair of the amine group is oxidized. Thus, an effect of suppressing the dissolution of the transition metal from the positive electrode at high temperature may be further improved, and high-temperature storage and cycle performance may be improved by mitigating self-discharge of the secondary battery.

Non-Aqueous Electrolyte Solution

Also, in the present invention, a non-aqueous electrolyte solution including the electrolyte solution additive for a secondary battery, which includes the compound represented by Formula 1, may be provided.

The non-aqueous electrolyte solution may further include a lithium salt, an organic solvent, and other additives.

(1) Additive

Since a description of the compound represented by Formula 1, which is included as the electrolyte solution additive of the present invention, overlaps with that described above, the description thereof will be omitted.

However, in consideration of an effect of forming a stable film on the surface of the electrode and an effect of scavenging the thermal decomposition product of the lithium salt, the electrolyte solution additive for a secondary battery may be included in an amount of 0.05 wt % to 3 wt %, particularly 0.1 wt % to 3 wt %, and more particularly 0.5 wt % to 1.5 wt % based on a total weight of the non-aqueous electrolyte solution. In a case in which the amount of the electrolyte solution additive for a secondary battery satisfies the above range, the dissolution of the transition metal of a positive electrode active material at high temperatures may be effectively suppressed, and excellent high-temperature durability may be achieved by effectively scavenging the thermal decomposition product of the lithium salt. If the amount of the electrolyte solution additive for a secondary battery is less than 0.05 wt %, the thermal decomposition product of the lithium salt may be initially scavenged during operation, but the scavenging effect may be insignificant as operation time increases, and the effect of suppressing the dissolution of the transition metal may be reduced due to an insignificant positive electrode protection effect. Also, if the amount of the additive is greater than 3 wt %, since a by-product and a side reaction due to the excessive amount of the additive occur, resistance of the secondary battery may be increased during high-temperature storage to degrade output characteristics.

Thus, in a case in which the amount of the electrolyte solution additive for a secondary battery satisfies the above range, the electrolyte solution additive may form a robust film on the surface of the positive electrode and simultaneously, may more effectively scavenge acids, such as HF and $PF_5$, decomposition products of the lithium salt, while suppressing disadvantages, such as the side reaction due to the additive, a reduction in capacity, and an increase in resistance, as much as possible.

(2) Lithium Salt

Any lithium salt typically used in an electrolyte solution for a lithium secondary battery may be used as the lithium salt without limitation, and, for example, the lithium salt may include Li+ as a cation, and may include at least one selected from the group consisting of F—, Cl—, Br—, I—, $NO_3$—, $N(CN)_2$—, $BF_4$—, $ClO_4$—, $B_{10}Cl_{10}$—, $AlCl_4$—, $AlO_4$—, $PF_6$—, $CF_3SO_3$—, $CH_3CO_2$—, $CF_3CO_2$—, $AsF_6$—, $SbF_6$—, $CH_3SO_3$—, $(CF_3CF_2SO_2)_2N$—, $(CF_3SO_2)_2N$—, $(FSO_2)_2N$—, $BF_2C_2O_4$—, $BC_4O_8$—, $PF_4C_2O_4$—, $PF_2C_4O_8$—, $(CF_3)_2PF_4$—, $(CF_3)_3PF_3$—, $(CF_3)_4PF_2$—, $(CF_3)_5PF$—, $(CF_3)_6P$—, $C_4F_9SO_3$—, $CF_3CF_2SO_3$—, $CF_3CF_2(CF_3)_2CO$—, $(CF_3SO_2)_2CH$—, $CF_3(CF_2)_7SO_3$, and SCN— as an anion.

Specifically, the lithium salt may include a single material selected from the group consisting of LiCl, LiBr, LiI, $LiBF_4$, $LiClO_4$, $LiB_{10}Cl_{10}$, $LiAlCl_4$, $LiAlO_4$, $LiPF_6$, $LiPF_3SO_3$, $LiCH_3CO_2$, $LiCF_3CO_2$, $LiAsF_6$, $LiSbF_6$, $LiCH_3SO_3$, LiFSI (lithium bis(fluorosulfonyl)imide, $LiN(SO_2F)_2$), LiBETI (lithium bis(perfluoroethanesulfonyl)imide, $LiN(SO_2CF_2CF_3)_2$), and LiTFSI (lithium bis(trifluoromethanesulfonyl)imide, $LiN(SO_2CF_3)_2$) or a mixture of two or more thereof. In addition to them, a lithium salt typically used in a non-aqueous electrolyte solution may be used without limitation.

The lithium salt may be appropriately changed in a normally usable range, but may be included in a concentration of 0.8 M to 4.0 M, for example, 1.0 M to 3.0 M in the electrolyte solution to obtain an optimum effect of forming a film for preventing corrosion of the surface of the electrode.

If the concentration of the lithium salt is less than 0.8 M, since mobility of lithium ions is reduced, an effect of improving low-temperature output and cycle characteristics during high-temperature storage is insignificant, and, if the concentration of the lithium salt is greater than 4.0 M, non-aqueous electrolyte solution impregnability may be reduced due to an excessive increase in viscosity of the non-aqueous electrolyte solution, and the film-forming effect may be reduced.

(3) Organic Solvent

Various organic solvents typically used in a lithium electrolyte solution may be used as the organic solvent without limitation, and, specifically, a type of the organic solvent is not limited as long as the organic solvent may minimize decomposition due to an oxidation reaction during charge and discharge of the secondary battery and may exhibit desired characteristics with the additive.

For example, a highly viscous cyclic carbonate-based organic solvent well dissociating the lithium salt in the electrolyte solution due to high permittivity may be used as the organic solvent. Also, in order to prepare an electrolyte solution having higher electrical conductivity, the above cyclic carbonate-based organic solvent may be mixed with a linear carbonate-based organic solvent in an appropriate ratio and used as the organic solvent.

The cyclic carbonate-based organic solvent is an organic solvent which may well dissociate the lithium salt in the electrolyte due to high permittivity as a highly viscous organic solvent, wherein specific examples of the cyclic carbonate-based organic solvent may be at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and, among them, the cyclic carbonate-based organic solvent may include at least one selected from ethylene carbonate and propylene carbonate (PC).

Also, the linear carbonate-based organic solvent is an organic solvent having low viscosity and low permittivity, wherein typical examples of the linear carbonate-based organic solvent may be at least one organic solvent selected from the group consisting of dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include ethyl methyl carbonate (EMC).

The cyclic carbonate organic solvent and the linear carbonate organic solvent may be mixed and used as the organic solvent of the present invention, and, in this case, the cyclic carbonate organic solvent and the linear carbonate organic solvent may be mixed in a volume ratio of 10:90 to 50:50, for example, 20:80 to 30:70.

Furthermore, in order to prepare an electrolyte solution having high ionic conductivity, the organic solvent may further include a linear ester-based organic solvent and/or a cyclic ester-based organic solvent with a low melting point and high stability at high temperatures in addition to the cyclic carbonate-based organic solvent and/or the linear carbonate-based organic solvent.

As a representative example, at least one organic solvent selected from the group consisting of dimethyl carbonate (DMC), diethyl carbonate (DEC), dipropyl carbonate, ethyl methyl carbonate (EMC), methylpropyl carbonate, and ethylpropyl carbonate may be used as the linear carbonate-based organic solvent, and the linear carbonate-based organic solvent may specifically include ethyl methyl carbonate (EMC).

Also, the cyclic ester-based organic solvent may include at least one organic solvent selected from the group consisting of γ-butyrolactone, γ-valerolactone, γ-caprolactone, θ-valerolactone, and ε-caprolactone.

A remainder excluding the amounts of components excluding the organic solvent in the non-aqueous electrolyte solution of the present invention, for example, the electrolyte solution additive, the lithium salt, and other additives to be described later, may all be the organic solvent unless otherwise stated.

(4) Other Additives

Also, the non-aqueous electrolyte solution for a lithium secondary battery of the present invention may further include additional other additives in addition to the compound represented by Formula 1, if necessary, in order to prevent the occurrence of the collapse of the negative electrode due to the decomposition of the non-aqueous electrolyte solution in a high power environment or to further improve low-temperature high rate discharge characteristics, high-temperature stability, overcharge prevention, and an effect of suppressing battery swelling at high temperature.

Examples of the other additives may be at least one selected from the group consisting of a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, and a lithium salt-based compound.

The cyclic carbonate-based compound, for example, may be vinylene carbonate (VC) or vinylethylene carbonate.

The halogen-substituted carbonate-based compound, for example, may be fluoroethylene carbonate (FEC).

The sultone-based compound, for example, may be at least one compound selected from the group consisting of 1,3-propane sultone (PS), 1,4-butane sultone, ethane sultone, 1,3-propene sultone (PRS), 1,4-butene sultone, and 1-methyl-1,3-propene sultone.

The sulfate-based compound, for example, may be ethylene sulfate (Esa), trimethylene sulfate (TMS), or methyl trimethylene sulfate (MTMS).

The phosphate-based compound, for example, may be at least one compound selected from the group consisting of lithium difluoro(bisoxalato)phosphate, lithium difluorophosphate, tris(trimethylsilyl)phosphate, tris(trimethylsilyl)phosphite, tris(2,2,2-trifluoroethyl)phosphate, and tris(trifluoroethyl)phosphite.

The borate-based compound, for example, may be tetraphenylborate or lithium oxalyldifluoroborate.

The nitrile-based compound, for example, may be at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The benzene-based compound, for example, may be fluorobenzene, the amine-based compound may be triethanolamine or ethylene diamine, and the silane-based compound may be tetravinylsilane.

The lithium salt-based compound is a compound different from the lithium salt included in the non-aqueous electrolyte solution, wherein the lithium salt-based compound may be at least one compound selected from the group consisting of $LiPO_2F_2$, LiODFB, LiBOB (lithium bis(oxalato) borate $(LiB(C_2O_4)_2)$), and $LiBF_4$.

In a case in which vinylene carbonate, vinylethylene carbonate, or succinonitrile, among these additional additives, is included, a more robust SEI may be formed on the surface of the negative electrode during an initial activation process of the secondary battery.

In a case in which the $LiBF_4$ is included, high-temperature stability of the secondary battery may be improved by suppressing the generation of gas which may be generated due to the decomposition of the electrolyte solution during high-temperature storage.

Two or more compounds may be mixed and used as the additive, and the additive may be included in an amount of 0.01 wt % to 50 wt %, particularly, 0.01 wt % to 10 wt %, and preferably 0.05 wt % to 5 wt % based on the total weight of the non-aqueous electrolyte solution. If the amount of the additional additive is less than 0.01 wt %, an effect of improving low-temperature output, high-temperature storage characteristics, and high-temperature life characteristics of the battery is insignificant, and, if the amount of the additional additive is greater than 50 wt %, a side reaction may excessively occur during charge and discharge of the battery due to the excessive amount of the additive. Particularly, when the excessive amount of the additives for forming an SEI is added, the additives for forming an SEI may not be sufficiently decomposed at high temperature so that they may be present in the form of an unreacted material or precipitates in the electrolyte solution at room temperature. Accordingly, a side reaction that degrades life or resistance characteristics of the secondary battery may occur.

Lithium Secondary Battery

Next, a lithium secondary battery according to the present invention will be described.

The lithium secondary battery according to the present invention includes a positive electrode, a negative electrode, a separator disposed between the positive electrode and the negative electrode, and a non-aqueous electrolyte solution, and, in this case, the non-aqueous electrolyte solution is the non-aqueous electrolyte solution according to the present invention. Since the non-aqueous electrolyte solution has been described above, a description thereof will be omitted and other components will be described below.

(1) Positive Electrode

The positive electrode according to the present invention may include a positive electrode active material layer including a positive electrode active material, and, if necessary, the positive electrode active material layer may further include a conductive agent and/or a binder.

The positive electrode active material is a compound capable of reversibly intercalating and deintercalating lithium, wherein the positive electrode active material may specifically include a lithium composite metal oxide including lithium and at least one metal selected from the group consisting of nickel (Ni), cobalt (Co), manganese (Mn), iron (Fe), and aluminum (Al).

More specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z1}Ni_ZO_4$ (where $0<Z<2$)), lithium-nickel-cobalt-based oxide (e.g., $LiNi_{1-Y1}Co_{Y1}O_2$ (where $0<Y1<1$)), lithium-manganese-cobalt-based oxide (e.g., $LiCo_{1-Y2}Mn_{Y2}O_2$ (where $0<Y2<1$), $LiMn_{2-z1}Co_{z1}O_4$ (where $0<Z1<2$)), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), or lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), and any one thereof or a compound of two or more thereof may be included.

Among these materials, in terms of the improvement of capacity characteristics and stability of the battery, the lithium composite metal oxide may include lithium nickel manganese cobalt oxide (e.g., $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.), and, particularly, in consideration of a significant improvement due to the control of type and content ratio of elements constituting the lithium composite metal oxide, high-nickel (Ni) $Li(Ni_{0.6}Mn_{0.2}Co_{0.2})O_2$, $Li(Ni_{0.7}Mn_{0.15}Co_{0.15})O_2$, $Li(Ni_{0.8}Mn_{0.1}Co_{0.1})O_2$, $Li(Ni_{0.8}Co_{0.15}Al_{0.05})O_2$, $Li(Ni_{0.86}Mn_{0.05}Co_{0.07}Al_{0.02})O_2$, or $Li(Ni_{0.90}Mn_{0.05}Co_{0.05})O_2$ may be used.

With respect to the above high-Ni positive electrode material, the dissolution of the transition metal may be intensified by acceleration of structural collapse of the positive electrode due to high-temperature exposure, and may be accelerated particularly when HF is present in the electrolyte solution, but, in a case in which an additive for scavenging a Lewis acid, for example, an additive capable of scavenging HF is added to the non-aqueous electrolyte solution as in the present invention, such a problem may be improved to further improve the high-temperature durability and stability of the secondary battery.

The positive electrode active material may be included in an amount of 80 wt % to 98 wt %, for example, 85 wt % to 98 wt % based on a total weight of the positive electrode active material layer. When the positive electrode active material is included in an amount within the above range, excellent capacity characteristics may be exhibited.

Next, the conductive agent is not particularly limited so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The conductive agent is typically added in an amount of 1 wt % to 30 wt %, or 0.1 wt % to 10 wt %, for example, 0.1 wt % to 5 wt % based on a total weight of a solid content in the positive electrode active material layer.

Next, the binder improves the adhesion between positive electrode active material particles and the adhesion between the positive electrode active material and a current collector.

Specific examples of the binder may be polyvinylidene fluoride (PVDF), polyvinylidene fluoride-hexafluoropropylene copolymer (PVDF-co-HFP), polyvinyl alcohol, polyacrylonitrile, carboxymethyl cellulose (CMC), starch, hydroxypropyl cellulose, regenerated cellulose, polyvinylpyrrolidone, poly tetrafluoroethylene, polyethylene, polypropylene, an ethylene-propylene-diene polymer, a sulfonated-ethylene-propylene-diene polymer, a styrene-butadiene rubber (SBR), a fluorine rubber, or various copolymers thereof, and any one thereof or a mixture of two or more thereof may be used. The binder may be included in an amount of 0.1 wt % to 15 wt %, for example, 0.1 wt % to 10 wt % based on the total weight of the positive electrode active material layer.

The positive electrode of the present invention as described above may be prepared by a method of preparing a positive electrode which is known in the art. For example, the positive electrode may be prepared by a method in which a positive electrode collector is coated with a positive electrode slurry, which is prepared by dissolving or dispersing the positive electrode active material, the binder, and/or the conductive agent in a solvent, dried, and then rolled to form a positive electrode active material layer, or a method in which the positive electrode active material layer is cast on a separate support, and a film separated from the support is then laminated on the positive electrode collector.

The positive electrode collector is not particularly limited as long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used. Also, the positive electrode collector may typically have a thickness of 3 μm to 500 μm, and microscopic irregularities may be formed on the surface of the collector to improve the adhesion of the positive electrode material. The positive electrode collector, for example, may be used in various shapes such as that of a film, a sheet, a foil, a net, a porous body, a foam body, a non-woven fabric body, and the like.

The solvent may be a solvent normally used in the art, and may include dimethyl sulfoxide (DMSO), isopropyl alcohol, N-methylpyrrolidone (NMP), acetone, or water, and any one thereof or a mixture of two or more thereof may be used. An amount of the solvent used may be sufficient if the positive electrode slurry may be adjusted to have appropriate viscosity in consideration of a coating thickness of the positive electrode material mixture, manufacturing yield, and workability, and is not particularly limited.

(2) Negative Electrode

Next, a negative electrode will be described.

The negative electrode according to the present invention includes a negative electrode active material layer including a negative electrode active material, and the negative electrode active material layer may further include a conductive agent and/or a binder, if necessary.

Various negative electrode active materials used in the art, for example, a carbon-based negative electrode active material, a silicon-based negative electrode active material, or a mixture thereof may be used as the negative electrode active material.

According to an embodiment, the negative electrode active material may include a carbon-based negative electrode active material, and, as the carbon-based negative electrode active material, various carbon-based negative electrode active materials used in the art, for example, a graphite-based materials such as natural graphite, artificial graphite, and Kish graphite; pyrolytic carbon, mesophase pitch based carbon fiber, meso-carbon microbeads, mesophase pitches, high-temperature sintered carbon such as petroleum or coal tar pitch derived cokes, soft carbon, and hard carbon may be used. A shape of the carbon-based negative electrode active material is not particularly limited, and materials of various shapes, such as an irregular shape, planar shape, flaky shape, spherical shape, or fibrous shape, may be used.

Preferably, the carbon-based negative electrode active material may include at least one of natural graphite and artificial graphite. More preferably, the carbon-based negative electrode active material may include natural graphite and artificial graphite. In a case in which the natural graphite and the artificial graphite are used together, adhesion with the current collector may be increased to suppress exfoliation of the active material.

According to another embodiment, the negative electrode active material may include a carbon-based negative electrode active material and a silicon-based negative electrode active material.

Specific examples of the carbon-based negative electrode active material are the same as described above.

The silicon-based negative electrode active material, for example, may include at least one selected from the group consisting of metallic silicon (Si), silicon oxide ($SiO_x$, where $0<x\leq 2$), silicon carbide (SiC), and a Si—Y alloy (where Y is an element selected from the group consisting of alkali metal, alkaline earth metal, a Group 13 element, a Group 14 element, transition metal, a rare earth element, and a combination thereof, and is not Si). The element Y may be selected from the group consisting of Mg, calcium (Ca), strontium (Sr), barium (Ba), radium (Ra), scandium (Sc), yttrium (Y), Ti, zirconium (Zr), hafnium (Hf), rutherfordium (Rf), V, niobium (Nb), Ta, dubnium (db), Cr, Mo, tungsten (W), seaborgium (Sg), technetium (Tc), rhenium (Re), bohrium (Bh), Fe, lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), Al, gallium (Ga), tin (Sn), indium (In), germanium (Ge), phosphorus (P), arsenic (As), antimony (Sb), bismuth (Bi), S, selenium (Se), tellurium (Te), polonium (Po), and a combination thereof.

Since the silicon-based negative electrode active material has higher capacity characteristics than the carbon-based negative electrode active material, better capacity characteristics may be obtained when the silicon-based negative electrode active material is further included. However, with respect to a negative electrode including the silicon-based negative electrode active material, it contains more oxygen (O)-rich (O-rich) components in the SEI than a graphite negative electrode, and the SEI containing the O-rich components tends to be more easily decomposed when a Lewis acid, such as HF or $PF_5$, is present in the electrolyte solution. Thus, with respect to the negative electrode including the silicon-based negative electrode active material, there is a need to suppress the formation of the Lewis acid, such as HF and $PF_5$, in the electrolyte solution or remove (or scavenge) the formed Lewis acid in order to stably maintain the SEI. Since the non-aqueous electrolyte according to the present invention includes the electrolyte solution additive capable of forming a stable film on the positive electrode and the negative electrode, it may effectively suppress the decomposition of the SEI when the negative electrode including the silicon-based negative electrode active material is used.

A mixing ratio of the silicon-based negative electrode active material the carbon-based negative electrode active material may be in a range of 3:97 to 99:1, for example, 5:95 to 15:85, as a weight ratio. In a case in which the mixing ratio of the silicon-based negative electrode active material to the carbon-based negative electrode active material satisfies the above range, since a volume expansion of the silicon-based negative electrode active material is suppressed while capacity characteristics are improved, excellent cycle performance may be secured.

The negative electrode active material may be included in an amount of 80 wt % to 99 wt % based on a total weight of the negative electrode active material layer. In a case in which the amount of the negative electrode active material satisfies the above range, excellent capacity characteristics and electrochemical properties may be obtained.

Next, the conductive agent is a component for further improving conductivity of the negative electrode active material, wherein the conductive agent may be added in an amount of 10 wt % or less, for example, 5 wt % or less based on the total weight of the negative electrode active material layer. Any conductive agent may be used without particular limitation so long as it has conductivity without causing adverse chemical changes in the battery, and, for example, a conductive material, such as: graphite such as natural graphite or artificial graphite; carbon black such as acetylene black, Ketjen black, channel black, furnace black, lamp black, and thermal black; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The binder is a component that assists in the binding between the conductive agent, the active material, and the current collector, wherein the binder is commonly added in an amount of 0.1 wt % to 10 wt % based on the total weight of the negative electrode active material layer. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene polymer, a sulfonated-ethylene-propylene-diene polymer, a styrene-butadiene rubber, a nitrile-butadiene rubber, a fluoro rubber, or various copolymers thereof.

The negative electrode may be prepared by a method of preparing a negative electrode which is known in the art. For example, the negative electrode may be prepared by a method in which a negative electrode collector is coated with a negative electrode slurry, which is prepared by dissolving or dispersing the negative electrode active material as well as optionally the binder and the conductive agent in a solvent, rolled and dried to form a negative electrode active material layer, or may be prepared by casting the negative electrode active material layer on a separate support and then laminating a film separated from the support on the negative electrode collector.

The negative electrode collector is not particularly limited as long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, or an aluminum-cadmium alloy may be used. Also, the negative electrode collector may typically have a thickness of 3 μm to 500 μm, and, similar to the positive electrode collector, microscopic irregularities may be formed on the surface of the collector to improve the adhesion of the negative electrode active material. The negative electrode collector, for example, may be used in various shapes such as that of a film, a sheet, a foil, a net, a porous body, a foam body, a non-woven fabric body, and the like.

The solvent may be a solvent normally used in the art, and may include dimethyl sulfoxide (DMSO), isopropyl alcohol, N-methylpyrrolidone (NMP), acetone, or water, and any one thereof or a mixture of two or more thereof may be used. An amount of the solvent used may be sufficient if the negative electrode slurry may be adjusted to have appropriate viscosity in consideration of a coating thickness of the negative electrode slurry, manufacturing yield, and workability, and is not particularly limited.

(3) Separator

The lithium secondary battery according to the present invention includes a separator between the positive electrode and the negative electrode.

The separator separates the negative electrode and the positive electrode and provides a movement path of lithium ions, wherein any separator may be used without particular limitation as long as it is typically used as a separator in a lithium secondary battery, and particularly, a separator having high moisture-retention ability for an electrolyte solution as well as low resistance to the transfer of electrolyte ions may be used.

Specifically, a porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, or a laminated structure having two or more layers thereof may be used. Also, a typical porous nonwoven fabric, for example, a nonwoven fabric formed of high melting point glass fibers or polyethylene terephthalate fibers may be used. Furthermore, a coated separator including a ceramic component or a polymer material may be used to secure heat resistance or mechanical strength, and the separator having a single layer or multilayer structure may be optionally used.

The lithium secondary battery according to the present invention as described above may be suitably used in portable devices, such as mobile phones, notebook computers, and digital cameras, and electric cars such as a hybrid electric vehicle (HEV).

Thus, according to another embodiment of the present invention, a battery module including the lithium secondary battery as a unit cell and a battery pack including the battery module are provided.

The battery module or the battery pack may be used as a power source of at least one medium and large sized device of a power tool; electric cars including an electric vehicle (EV), a hybrid electric vehicle (HEV), and a plug-in hybrid electric vehicle (PHEV); or a power storage system.

A shape of the lithium secondary battery of the present invention is not particularly limited, but a cylindrical type using a can, a prismatic type, a pouch type, or a coin type may be used.

The lithium secondary battery according to the present invention may not only be used in a battery cell that is used as a power source of a small device, but may also be used as a unit cell in a medium and large sized battery module including a plurality of battery cells.

Hereinafter, the present invention will be described in detail, according to specific examples.

EXAMPLES

Example 1

(Non-Aqueous Electrolyte Solution Preparation)

After $LiPF_6$ and LiFSI were dissolved in 99.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M and a concentration of the LiFSI was 0.2 M, a non-aqueous electrolyte solution was prepared by adding 0.5 g of the compound represented by Formula 1a as an additive.

Positive Electrode Preparation

A lithium nickel-manganese-aluminum oxide ($Li(Ni_{0.86}Mn_{0.05}Co_{0.07}Al_{0.02})O_2$) as positive electrode active material particles, carbon black as a conductive agent, and polyvinylidene fluoride (PVDF), as a binder, were added to N-methyl-2-pyrrolidone (NMP), as a solvent, at a weight ratio of 90:5:5 to prepare a positive electrode active material slurry (solid content 48 wt %). A 100 μm thick positive electrode collector (Al thin film) was coated with the positive electrode active material slurry, dried, and then roll-pressed to prepare a positive electrode.

Negative Electrode Preparation

A negative electrode active material (artificial graphite: SiO=94.5:5.5 weight ratio), PVDF as a binder, and carbon black, as a conductive agent, were added to NMP, as a solvent, at a weight ratio of 95:2:3 to prepare a negative electrode active material slurry (solid content: 70 wt %). A 90 μm thick negative electrode collector (Cu thin film) was coated with the negative electrode active material slurry, dried, and then roll-pressed to prepare a negative electrode.

Secondary Battery Preparation

After an electrode assembly was prepared by a conventional method of sequentially stacking a polyethylene porous film with the positive electrode and negative electrode prepared by the above-described methods, the electrode assembly was put in a pouch-type secondary battery case, and the above-prepared non-aqueous electrolyte solution was injected thereinto to prepare a lithium secondary battery.

Example 2

A lithium secondary battery was prepared in the same manner as in Example 1 except that, after $LiPF_6$ and LiFSI were dissolved in 99 g of a non-aqueous organic solvent such that a concentration of the $LiPF_6$ was 1.0 M and a concentration of the LiFSI was 0.2 M, a non-aqueous electrolyte solution was prepared by adding 1.0 g of the compound represented by Formula 1a as an additive.

Example 3

A lithium secondary battery was prepared in the same manner as in Example 1 except that, after $LiPF_6$ and LiFSI were dissolved in 99.9 g of a non-aqueous organic solvent such that a concentration of the $LiPF_6$ was 1.0 M and a concentration of the LiFSI was 0.2 M, a non-aqueous electrolyte solution was prepared by adding 0.1 g of the compound represented by Formula 1a as an additive.

Example 4

A lithium secondary battery was prepared in the same manner as in Example 1 except that, after $LiPF_6$ and LiFSI were dissolved in 98.5 g of a non-aqueous organic solvent such that a concentration of the $LiPF_6$ was 1.0 M and a concentration of the LiFSI was 0.2 M, a non-aqueous electrolyte solution was prepared by adding 1.5 g of the compound represented by Formula 1a as an additive.

Example 5

A lithium secondary battery was prepared in the same manner as in Example 1 except that, after $LiPF_6$ and LiFSI were dissolved in 98 g of a non-aqueous organic solvent such that a concentration of the $LiPF_6$ was 1.0 M and a concentration of the LiFSI was 0.2 M, a non-aqueous electrolyte solution was prepared by adding 2.0 g of the compound represented by Formula 1a as an additive.

Example 6

A lithium secondary battery was prepared in the same manner as in Example 1 except that, after $LiPF_6$ and LiFSI were dissolved in 97 g of a non-aqueous organic solvent such that a concentration of the $LiPF_6$ was 1.0 M and a concentration of the LiFSI was 0.2 M, a non-aqueous electrolyte solution was prepared by adding 3.0 g of the compound represented by Formula 1a as an additive.

Example 7

A lithium secondary battery was prepared in the same manner as in Example 1 except that, after $LiPF_6$ and LiFSI were dissolved in 96 g of a non-aqueous organic solvent such that a concentration of the $LiPF_6$ was 1.0 M and a concentration of the LiFSI was 0.2 M, a non-aqueous electrolyte solution was prepared by adding 4.0 g of the compound represented by Formula 1a as an additive.

Comparative Example 1

A lithium secondary battery was prepared in the same manner as in Example 1 except that, after $LiPF_6$ and LiFSI were dissolved in 99.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M and a concentration of the LiFSI was 0.2 M, an additive was not added to prepare a non-aqueous electrolyte solution.

Comparative Example 2

A lithium secondary battery was prepared in the same manner as in Example 1 except that, after $LiPF_6$ and LiFSI were dissolved in 99.5 g of a non-aqueous organic solvent such that a concentration of the $LiPF_6$ was 1.0 M and a concentration of the LiFSI was 0.2 M, a non-aqueous electrolyte solution was prepared by adding 0.5 g of a compound represented by the following Formula 2, instead of the compound represented by Formula 1a, as an additive.

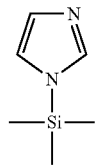

[Formula 2]

Comparative Example 3

A lithium secondary battery was prepared in the same manner as in Example 1 except that, after $LiPF_6$ and LiFSI were dissolved in 99.5 g of a non-aqueous organic solvent such that a concentration of the $LiPF_6$ was 1.0 M and a concentration of the LiFSI was 0.2 M, a non-aqueous electrolyte solution was prepared by adding 0.5 g of a compound represented by the following Formula 3, instead of the compound represented by Formula 1a, as an additive.

[Formula 3]

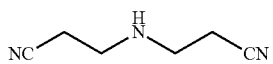

EXPERIMENTAL EXAMPLES

Experimental Example 1: Evaluation of Ionic Conductivity of Non-aqueous Electrolyte Solution Ionic conductivities of the non-aqueous electrolyte solutions prepared in Examples 1 to 7 were measured using a probe-type ionic conductivity measurement device. The results thereof are presented in Table 1 below.

Experimental Example 2: Initial Resistance Evaluation

After each of the lithium secondary batteries prepared in Examples 1 to 7 was charged at 0.33 C rate to 4.2 V under a constant current/constant voltage condition at room temperature (25° C.), each lithium secondary battery was discharged to a DOD (depth of discharge) of 50% to adjust a state of charge (SOC) to 50% and then discharged at 2.5 C rate for 10 seconds, and initial resistance was measured using PNE-0506 charge/discharge equipment (manufacturer: PNE solution). The results thereof are listed in Table 1 below.

TABLE 1

| | Additive | | Initial resistance (mohm) | Ionic conductivity (mS/cm) |
|---|---|---|---|---|
| | Formula | Amount (wt %) | | |
| Example 1 | 1a | 0.5 | 40.05 | 8.68 |
| Example 2 | 1a | 1.0 | 41.21 | 8.65 |
| Example 3 | 1a | 0.1 | 39.45 | 8.70 |
| Example 4 | 1a | 1.5 | 42.11 | 8.61 |
| Example 5 | 1a | 2.0 | 42.65 | 8.55 |
| Example 6 | 1a | 3.0 | 42.94 | 8.23 |
| Example 7 | 1a | 4.0 | 44.39 | 7.87 |

Referring to Table 1, with respect to the secondary battery of Example 7 including an excessive amount of the additive, initial resistance was increased, but ionic conductivity was decreased in comparison to those of the secondary batteries of Examples 1 to 6. From these results, since the secondary battery of Example 7 was difficult to maintain stable internal resistance in comparison to the secondary batteries of Examples 1 to 6, rate performance of the finally prepared secondary battery may be degraded.

Experimental Example 3. Characteristics Evaluation After High-temperature Storage (1)

After each of the lithium secondary batteries prepared in Examples 1 to 6 and the lithium secondary batteries prepared in Comparative Examples 1 to 3 was fully charged (state of charge (SOC) of 100%) at 0.33 C rate to 4.2 V and a cut-off current of 50 mA under a constant current/constant voltage condition at room temperature (25° C.) and discharged at 0.33 C rate under a constant current condition to 3 V, discharge capacity before high-temperature storage was measured using PNE-0506 charge/discharge equipment (manufacturer: PNE solution).

Then, after each lithium secondary battery was stored at 60° C. for 2 weeks, capacity after high-temperature storage was measured for each lithium secondary battery, and a high-temperature capacity retention (%) was then calculated using [Equation 1] below. The results thereof are listed in Table 2 below.

Capacity retention (%):(discharge capacity after 2 weeks high-temperature storage at 60° C./discharge capacity before high-temperature storage)×100  [Equation 1]

Experimental Example 4. Characteristics Evaluation After High-temperature Storage (2)

After each of the lithium secondary batteries prepared in Examples 1 to 6 and the lithium secondary batteries prepared in Comparative Examples 1 to 3 was charged at 0.33 C rate to 4.2 V under a constant current/constant voltage condition at room temperature (25° C.), each lithium secondary battery was discharged to a DOD (depth of discharge) of 50% to adjust a SOC to 50% and then discharged at 2.5 C rate for 10 seconds, and initial resistance was measured using PNE-0506 charge/discharge equipment (manufacturer: PNE solution).

Then, after each lithium secondary battery was stored at 60° C. for 2 weeks, resistance of the lithium secondary battery was measured, and a resistance increase rate (%) was calculated using [Equation 2] below. The results thereof are listed in Table 2 below.

Resistance increase rate (%)={(resistance after 2 weeks high-temperature storage at 60° C.−resistance before high-temperature storage)/resistance before high-temperature storage}×100  [Equation 2]

TABLE 2

| | Additive | | Capacity retention (%) | Resistance increase rate (%) |
|---|---|---|---|---|
| | Formula | Amount (wt %) | | |
| Example 1 | 1a | 0.5 | 99.69 | 1.38 |
| Example 2 | 1a | 1.0 | 99.74 | 0.56 |
| Example 3 | 1a | 0.1 | 99.12 | 2.25 |
| Example 4 | 1a | 1.5 | 99.77 | 0.49 |
| Example 5 | 1a | 2.0 | 99.81 | 0.35 |
| Example 6 | 1a | 3.0 | 99.82 | 0.31 |
| Comparative Example 1 | — | 0 | 98.69 | 5.10 |
| Comparative Example 2 | 2 | 2 | 98.90 | 4.21 |
| Comparative Example 3 | 3 | 2 | 95.34 | 10.24 |

Referring to Table 2, with respect to the lithium secondary batteries of Examples 1 to 6 which respectively included the non-aqueous electrolyte solutions including the additive of the present invention, it may be understood that capacity retentions and resistance increase rates after high-temperature storage were all improved in comparison to those of the secondary battery of Comparative Example 1 including the non-aqueous electrolyte solution without the additive and those of the secondary batteries of Comparative Examples 2 and 3 which respectively included the non-aqueous electrolyte solution including the compound of Formula 2 as an additive and the non-aqueous electrolyte solution including the compound of Formula 3 as an additive.

Experimental Example 5: High-temperature Cycle Characteristics Evaluation

That each of the lithium secondary batteries prepared in Examples 1 to 6 and Comparative Examples 1 to 3 was charged at 0.33 C rate to 4.2 V under a constant current/constant voltage condition at 45° C. and then discharged at 0.33 C rate under a constant current condition to 3 V was defined as one cycle and capacity retention (%) and resistance increase rate (%) were measured after 50 cycles of charge and discharge were performed. The capacity retention (%) was calculated according to [Equation 3] below, and the resistance increase rate (%) was calculated according to [Equation 4] below. Measurement results are listed in Table 3 below.

Capacity retention (%)=(discharge capacity after 50 cycles/discharge capacity after 1 cycle)×100  [Equation 3]

Resistance increase rate (%)={(resistance after 50 cycles−resistance after 1 cycle)/resistance after 1 cycle}×100  [Equation 4]

TABLE 3

| | Additive | | Capacity retention (%) | Resistance increase rate (%) |
|---|---|---|---|---|
| | Formula | Amount (wt %) | | |
| Example 1 | 1a | 0.5 | 99.11 | 0.31 |
| Example 2 | 1a | 1.0 | 99.54 | 0.12 |
| Example 3 | 1a | 0.1 | 98.45 | 0.54 |
| Example 4 | 1a | 1.5 | 99.60 | 0.30 |
| Example 5 | 1a | 2.0 | 99.65 | 0.25 |
| Example 6 | 1a | 3.0 | 99.78 | 0.22 |
| Comparative Example 1 | — | 0 | 97.78 | 30.02 |
| Comparative Example 2 | 2 | 2 | 98.12 | 5.98 |
| Comparative Example 3 | 3 | 2 | 97.21 | 9.54 |

Referring to Table 3, with respect to the lithium secondary batteries of Examples 1 to 6 which respectively included the non-aqueous electrolyte solutions including the additive of the present invention, it may be understood that capacity retentions and resistance increase rates after high-temperature cycles were all improved in comparison to those of the secondary battery of Comparative Example 1 including the non-aqueous electrolyte solution without using the additive and those of the secondary batteries of Comparative Examples 2 and 3 which respectively included the non-aqueous electrolyte solution including the compound of Formula 2 as an additive and the non-aqueous electrolyte solution including the compound of Formula 3 as an additive.

Experimental Example 6: Evaluation of Voltage Drop Rate (%) After High-temperature Storage After each of the lithium secondary batteries prepared in Examples 1 to 6 and the lithium secondary batteries prepared in Comparative Examples 1 to 3 was fully charged (SOC of 100%) at 0.33 C rate to 4.2 V and a cut-off current of 50 mA under a constant current/constant voltage condition at room temperature (25° C.), an initial voltage (4.2 V) before high-temperature storage was measured using PNE-0506 charge/discharge equipment (manufacturer: PNE solution).

Subsequently, after each lithium secondary battery was stored at a high temperature of 72° C. for 60 days, a voltage drop rate (%) was evaluated. The voltage drop rate (%) was calculated according to [Equation 5] below. Measurement results are listed in Table 4 below.

Voltage Drop rate (%)={(voltage after 60 days high-temperature storage−initial voltage)/initial voltage}×100  [Equation 5]

TABLE 4

| | Additive | | Voltage after 60 days | Voltage drop rate (%) |
|---|---|---|---|---|
| | Formula | Amount (wt %) | | |
| Example 1 | 1a | 0.5 | 4.153 | 1.12 |
| Example 2 | 1a | 1.0 | 4.156 | 1.05 |
| Example 3 | 1a | 0.1 | 4.135 | 1.55 |
| Example 4 | 1a | 1.5 | 4.164 | 0.86 |
| Example 5 | 1a | 2.0 | 4.169 | 0.74 |
| Example 6 | 1a | 3.0 | 4.170 | 0.71 |
| Comparative Example 1 | — | 0 | 4.013 | 4.45 |
| Comparative Example 2 | 2 | 2 | 4.115 | 2.02 |
| Comparative Example 3 | 3 | 2 | 4.025 | 4.17 |

The expression "voltage drop" denotes a phenomenon in which, when transition metal dissolved from a positive electrode consumes electrons while being reduced at a negative electrode side or when a film (SEI) is not properly formed on a negative electrode, an electrolyte solution increases a voltage of the negative electrode while being easily reductively decomposed to drop a voltage of a full cell.

Referring to Table 4, with respect to the lithium secondary batteries of Examples 1 to 6 which respectively included the non-aqueous electrolyte solutions including the additive of the present invention, it may be understood that voltage drop rates (%) after high-temperature storage were all improved in comparison to that of the secondary battery of Comparative Example 1 including the non-aqueous electrolyte solution without using an additive and those of the secondary batteries of Comparative Examples 2 and 3 which respectively included the non-aqueous electrolyte solution including the compound of Formula 2 as an additive and the non-aqueous electrolyte solution including the compound of Formula 3 as an additive.

The invention claimed is:

1. A non-aqueous electrolyte solution for a lithium secondary battery, the non-aqueous electrolyte solution comprising an electrolyte solution additive comprising a compound represented by Formula 1:

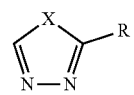

[Formula 1]

wherein, in Formula 1,

X is oxygen (O) or sulfur(S), and

R is a substituted or unsubstituted alkyl group having 1 to 5 carbon atoms or N (R$_1$)$_2$, wherein R$_1$ is hydrogen or a substituted or unsubstituted alkyl group having 1 to 5 carbon atoms.

2. The non-aqueous electrolyte solution of claim 1, wherein, in Formula 1, X is S, and R is a substituted or unsubstituted alkyl group having 1 to 3 carbon atoms or N $(R_1)_2$, wherein $R_1$ is hydrogen or a substituted or unsubstituted alkyl group having 1 to 3 carbon atoms.

3. The non-aqueous electrolyte solution of claim 1, wherein, in Formula 1, X is S, and R is N $(R_1)_2$, wherein $R_1$ is hydrogen or a substituted or unsubstituted alkyl group having 1 to 5 carbon atoms.

4. The non-aqueous electrolyte solution of claim 1, wherein the compound represented by Formula 1 comprises a compound represented by Formula 1a:

[Formula 1a]

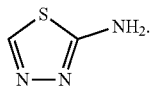

5. The non-aqueous electrolyte solution of claim 1, wherein the electrolyte solution additive is included in an amount of 0.05 wt % to 3 wt % based on a total weight of the non-aqueous electrolyte solution.

6. The non-aqueous electrolyte solution of claim 5, wherein the electrolyte solution additive is present in an amount of 0.1 wt % to 3 wt % based on the total weight of the non-aqueous electrolyte solution.

7. The non-aqueous electrolyte solution of claim 1, further comprising a lithium salt and an organic solvent.

8. The non-aqueous electrolyte solution of claim 1, further comprising at least one second additive selected of a cyclic carbonate-based compound, a halogen-substituted carbonate-based compound, a sultone-based compound, a sulfate-based compound, a phosphate-based compound, a borate-based compound, a nitrile-based compound, an amine-based compound, a silane-based compound, or a lithium salt-based compound.

9. A lithium secondary battery, comprising:
a positive electrode;
a negative electrode;
a separator disposed between the negative electrode and the positive electrode; and
the non-aqueous electrolyte solution of claim 1.

* * * * *